United States Patent
Sorensen

Patent Number: 5,087,763
Date of Patent: Feb. 11, 1992

[54] HYDROFORMYLATION PROCESS

[75] Inventor: Kirk D. Sorensen, Charleston, W. Va.

[73] Assignee: Union Carbide Chemicals & Plastics Technology Corporation, Danbury, Conn.

[21] Appl. No.: 611,081

[22] Filed: Nov. 9, 1990

[51] Int. Cl.$^5$ .................. C07C 45/78; C07C 45/50
[52] U.S. Cl. .................. 568/492; 568/451; 568/454
[58] Field of Search .............. 568/451, 454, 492

[56] References Cited

U.S. PATENT DOCUMENTS

| | | | |
|---|---|---|---|
| 3,527,809 | 8/1970 | Pruett et al. | 260/604 |
| 4,148,830 | 4/1979 | Pruett et al. | 260/604 HF |
| 4,210,426 | 7/1980 | Sridhar | 55/68 |
| 4,482,748 | 11/1984 | Booth | 568/454 |
| 4,491,675 | 1/1985 | Abatjoglou et al. | 568/454 |
| 4,496,768 | 1/1985 | Dennis et al. | 568/454 |
| 4,523,036 | 6/1985 | Cornils et al. | 568/454 |
| 4,533,757 | 8/1985 | Kummer et al. | 568/454 |
| 4,577,043 | 4/1986 | Kalbfel | 568/454 |
| 4,593,127 | 6/1986 | Bunning | 568/454 |
| 4,599,206 | 7/1986 | Billig et al. | 568/454 |
| 4,613,701 | 9/1986 | Strong | 568/454 |
| 4,668,651 | 5/1987 | Billig et al. | 568/454 |
| 4,711,648 | 12/1987 | Kaokul | 55/73 |
| 4,716,250 | 12/1987 | Abatjoglou et al. | 568/454 |
| 4,717,775 | 1/1988 | Billig et al. | 568/454 |
| 4,731,486 | 3/1988 | Abatjoglou et al. | 568/484 |
| 4,769,498 | 9/1988 | Billig et al. | 568/454 |
| 4,774,361 | 9/1988 | Maher et al. | 568/454 |
| 4,827,043 | 5/1989 | Butler | 568/492 |
| 5,001,274 | 3/1991 | Bunning | |

OTHER PUBLICATIONS

"Indications", Winter 1982/83, The International Journal published by the Public Affairs Dept. of the Davy Corporation, London, England.

"Oxo Alcohol Plant Debottlenecking Using New Rhodium Technology" by R. M. Tudor, North Western Branch Symposium Papers, 1979, No. 3, pp. 6.1 to 6.11, Institution of Chem. Eng., England.

"Chemical Engineers' Handbook", 5th Ed., Perry & Chilton, 1973, pp. 14–10, 14–11, 14–13 and 18–3.

"Mass-Transfer Operations", 2nd Ed. R.E. Treybal, 1968, Chapter 8, Gas Absorption, p. 220.

*Primary Examiner*—Werren B. Lone
*Attorney, Agent, or Firm*—Reynold J. Finnegan

[57] ABSTRACT

An improved liquid recycle rhodium-catalyzed hydroformylation process wherein the improvement comprises recovering unreacted olefin contained in a vent gas of the process and recycling said unreacted olefin to the hydroformylation reaction medium.

7 Claims, 1 Drawing Sheet

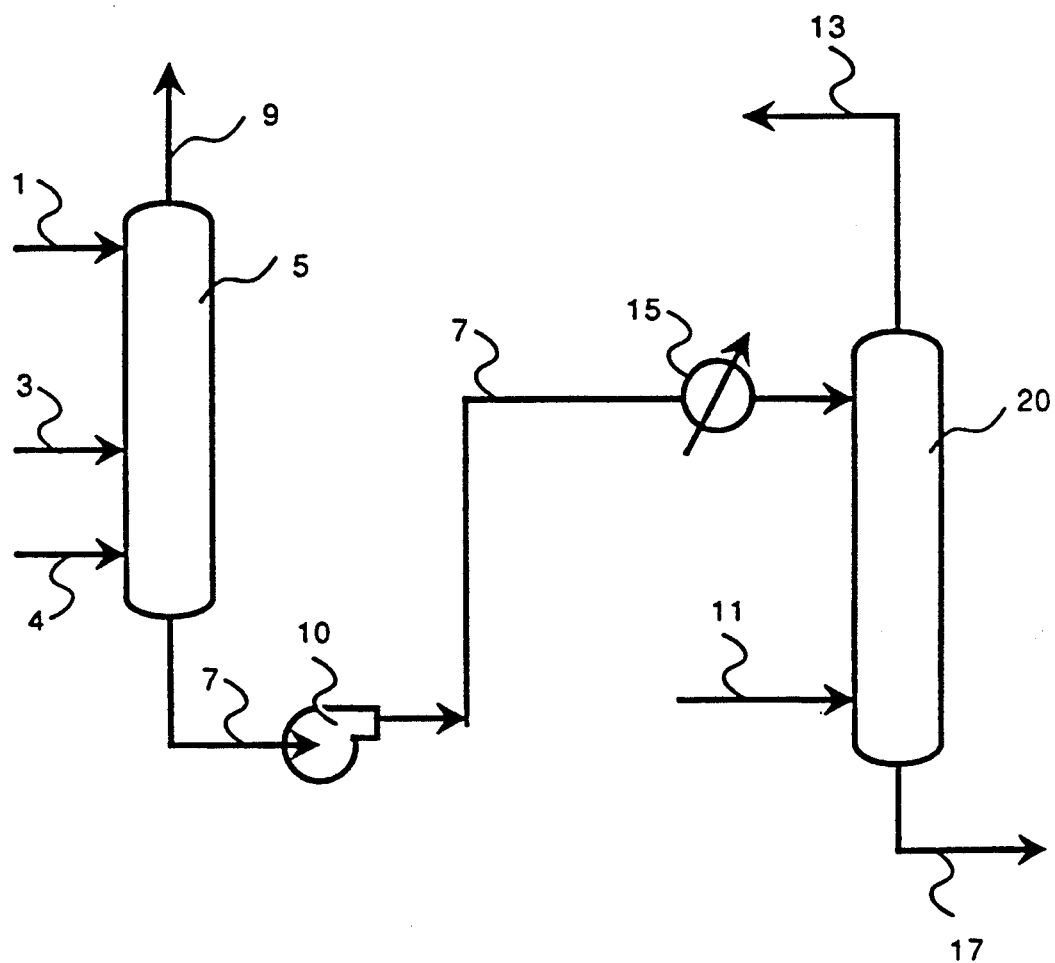

HYDROFORMYLATION PROCESS

FIELD OF THE INVENTION

This invention relates to an improved process for hydroformylating an olefin with carbon monoxide and hydrogen in the presence of a rhodium catalyst. More particularly this invention relates to an improved liquid recycle rhodium-catalyzed hydroformylation process wherein the improvement comprises recovering unreacted olefin contained in a vent gas of the process and recycling said unreacted olefin to the hydroformylation reaction medium in an economical and efficient manner.

BACKGROUND OF THE INVENTION

Methods for producing aldehydes by the hydroformylation of an olefinically unsaturated organic compound with carbon monoxide and hydrogen (more commonly referred to as synthesis or syn gas) in the presence of a rhodium-phosphorus complex catalyst and free phosphorus ligand are well known in the art as seen; e.g., by the basic low pressure oxo hydroformylation process of U.S. Pat. No. 3,527,809 and the rhodium-catalyzed liquid recycle hydroformylation process of U.S. Pat. No. 4,148,830.

In U.S. Pat. No. 4,148,830 (the '830 Patent) it is disclosed that catalyst life can be enhanced and product yield improved by employing as a catalyst solvent for rhodium-catalyzed hydroformylation, higher boiling aldehyde condensation products (e.g. dimers, trimers and tetramers), as defined therein. It was also found that the rhodium catalyst could be continuously or intermittently recycled to the hydroformylation reaction zone without significant loss of rhodium, catalyst life, reaction rates and efficiency.

Accordingly, the '830 Patent disclosed that liquid effluent from the reaction zone containing catalyst, solvent and gases, is processed to strip and recover the aldehyde product. During this procedure some lights, e.g., hydrogen, carbon monoxide, unreacted olefin, corresponding alkane, and other by-product and inert gases dissolved in the reactor effluent are removed by reducing pressure on the effluent stream to flash off such gases. The desired aldehyde product is then recovered from the effluent and the remaining liquid residue fraction of unrecovered aldehydic product, catalyst and high boiling condensation product is recycled to the reactor. Thus, this process is often referred to as a liquid-recycle hydroformylation process (or "liquid recycle process").

Further to control the total reactor pressure in a liquid recycle process due to build up of inerts and the like, a gaseous purge is generally taken from the liquid recycle hydroformylation reactor, where excess hydrogen, carbon monoxide, unreacted olefin, inerts and alkane by-products, such as propane in the case of hydroformylating propylene, are vented as off-gases.

In addition, during the product separation step in a liquid recycle process, some gases, primarily unreacted olefin and alkane by-product, which remain dissolved in the liquid catalyst-containing effluent, are separated along with the desired aldehyde product. A portion of such separated gases are condensed with the desired aldehyde product. The remaining separated gases can be purged from the system.

Thus, the outright loss of unreacted olefin and syn gas components by purging in such liquid recycle processes could amount to a significant economic disadvantage over the life of commercial continuous hydroformylation operations designed to produce tens of millions of pounds of aldehyde per year, and various methods have been proposed to prevent this.

For instance, U.S. Pat. No. 4,593,127 illustrates a typical liquid recycle rhodium-catalyzed hydroformylation process as seen by the primary reactor system of FIG. 1 and the secondary reactor system of FIG. 2 of the drawings of said patent. Note that the vent gas line 28 in FIG. 1 that originates in the reactor headspace serves to conduct unreacted olefin and syn gas to the decoupled secondary reactor system of FIG. 1, while the gas vent lines 18 and 24 of said FIG. 1 each require compressors 20 and 21, if the unreacted olefin and syn gas are to be recycled to the hydroformylation reactor. On the other hand, the unreacted olefin and other light gases as seen by vent gas lines 91 and 92 of the secondary reactor system of FIG. 2 of said U.S. Pat. No 4,593,127 are given up as lost (e.g., burned as fuel). While it is taught that the vent gas line 91 may be recycled to the reactor, if desired, obviously such recycling will require the efforts of a compressor such as shown by compressors 20 and 21 in the primary reactor system of FIG. 1. Accordingly, while U.S. Pat. No 4,593,127 does teach the importance of recovering and recycling unreacted olefin from the vent gases of a liquid recycle hydroformylation process, such is taught to be accomplished by the employment of costly energy inefficient compressors and/or extensive additional processing equipment (e.g., the secondary reactor system of FIG. 1).

U.S. Pat. No. 4,210,426, discloses recovering propene and propane from the off-gas of a process involving the hydroformylation of propene by contacting the off-gas with a liquid absorbent comprising at least one of the liquid substances formed during the hydroformylation, e.g., n-and/or iso-butyraldehyde, to absorb the propene and propane and thereafter subsequently desorbing these gases from the absorbent by lowering the pressure and/or raising the temperature. The propene and propane may then be separated by distillation. Alternatively, it is possible to separate off only the propene from the absorbent by combining the desorption with fractional distillation and the propane subsequently removed from the absorbent by distillation. Preferably the propene is recycled to the reactor and the absorbent to the absorption column. Note, however, that the recovery system of U.S. Pat. No. 4,210,466 promotes the employment of high absorption pressures (column 2, lines 4-33) and illustrates the need for extensive processing equipment (three independent recovery columns).

U.S. application Ser. No. 370,806 filed June 23, 1989, now U.S. Pat. No 5,001,274 patent Mar. 19, 1991, discloses recovering absorbable gaseous components, such as unreacted olefin and product aldehyde, contained, e.g., in the vent gas of the reactor of liquid recycle rhodium-catalyzed hydroformylation process, by contacting said vent gas with the hydroformylation catalyst solution that is being recycled to the reactor after its separation from the product aldehyde, so as to absorb said gaseous components therein. The resulting catalyst solution is then returned directly to the hydroformylation reactor without any desorption or separation of the gaseous unreacted olefin and product aldehyde. However, as in any system that employs the rhodium-catalyst solution that is being recycled to the reactor there is always a danger of losing rhodium, e.g., via the purge lines 28, 31a or 31b from the scrubbers shown in the drawing of said U.S. Pat. No. 5,001,274.

U.S. Pat. No. 4,827,043 discloses purifying gas streams, e.g., syn gas, by contacting them with at least a portion of the aldehyde containing product stream obtained from a gas recycle hydroformylation process prior to introducing the syn gas feed into the hydroformylation reaction zone. The process is said to remove undesirable impurities from the syn gas, e.g., oxygen, sulfur bearing lubricating oil and iron carbonyl. Said patent also discloses (Example 5) recovering and recycling unreacted propylene from crude hydroformylation aldehyde product streams, in the same manner as disclosed in INDICATIONS, Winter 1982/83, the International Journal of Davy McKee, pp. 20 to 28 published by the public affairs department of the Davy Corporation, London, England.

SUMMARY OF THE INVENTION

The present invention provides a process for recovering unreacted olefin, from one or more gaseous streams vented from, or otherwise existing in, a liquid recycle rhodium catalyzed hydroformylation reaction system, by (1) contacting said gaseous stream or streams with the liquid aldehyde product produced by said hydroformylation so as to absorb the unreacted olefin contained therein; (2) stripping said unreacted olefin gas from the resultant absorbent liquid containing the absorbed unreacted olefin by passing synthesis gas ($CO + H_2$) through said resultant absorbent liquid to obtain a gaseous mixture of synthesis gas and the stripped unreacted olefin; and (3) recycling said gaseous mixture so obtained to the hydroformylation reactor of said hydroformylation process.

Thus, it is an object of this invention to provide an improved liquid recycle rhodium-catalyzed hydroformylation process wherein the unreacted olefin of a gaseous vent stream of said hydroformylation can be recovered and recycled to the hydroformylation reactor of said process in a most simple, efficient and economical manner. Other objects and advantages of this invention will become readily apparent from the following written description and appended claims.

Accordingly, a generic aspect of this invention may be described as an improved liquid recycle rhodium-catalyzed hydroformylation process for producing $C_3$ to $C_5$ aldehydes, wherein an olefin containing from 2 to 4 carbon atoms, carbon monoxide and hydrogen are reacted in the presence of a solubilized rhodium-phosphorus complex catalyst, free phosphorus ligand and higher boiling aldehyde condensation by-products, to produce an aldehyde product selected from the class consisting of propanal, a mixture of n-butanal and isobutanal, and a mixture of n-pentanal and branched-chain pentanals, and wherein a gaseous effluent comprising unreacted olefin, carbon monoxide and hydrogen gases is vented from the process, the improvement which comprises recovering said unreacted olefin from said vent gas by (1) absorbing the unreacted olefin in an absorbent comprising the liquid aldehyde product produced by said hydroformylation process; (2) stripping the absorbed unreacted olefin from said absorbent by passing synthesis gas through the resultant absorbent containing said unreacted olefin to obtain a gaseous mixture of synthesis gas and the stripped unreacted olefin; and (3) recycling said gaseous mixture to the hydroformylation reactor of said hydroformylation process.

BRIEF DESCRIPTION OF THE DRAWING

The drawing is a schematic flow diagram of the subject invention illustrating the embodiment of an apparatus, e.g., an absorber also commonly referred to as a scrubber, for effecting the recovery of unreacted olefin from a vent gas of the hydroformylation process via absorption, along with an apparatus, e.g., a gas stripper, for stripping absorbed unreacted olefin gas from the resultant absorbent liquid via the use of synthesis gas and recycling said gases to the hydroformylation reactor.

DESCRIPTION OF THE PREFERRED EMBODIMENTS

While this invention is considered to be applicable for improving any continuous gas and/or liquid recycle hydroformylation process it has been found especially suitable for improving any conventional continuous liquid recycle rhodium-phosphorus complex catalyzed hydroformylation process for producing aldehydes, which process is conducted in the presence of free phosphorus ligand. Such liquid recycle hydroformylation (oxo) processes and the conditions thereof are well known in the art as illustrated, e.g., by the continuous liquid recycle processes of, e.g., U.S. Pat. Nos. 4,148,830 and 4,593,127 and U.S. Pat. No. 5,001,274 filed June 23, 1989, and in general, involve the production of aldehydes by reacting an olefinic compound with hydrogen and carbon monoxide in a liquid reaction medium which contains a soluble rhodium-organophosphorus complex catalyst, free organophosphorus ligand and higher boiling aldehyde condensation by-products.

Of course, it is to be understood that the particular manner in which the hydroformylation reaction is carried out and particular hydroformylation reaction conditions employed are not critical to the subject invention and may be varied widely and tailored to meet individual needs and to produce the particular aldehyde product desired.

Accordingly, the olefinic starting material reactants encompassed by the process of this invention can be terminally or internally unsaturated and be of straight-chain or branched-chain alkylene structure. Such olefins may have from 2 to 30 carbon atoms, but more preferably contain from 2 to 4 carbon atoms.

Illustrative preferred olefins are ethylene, propylene, 1-butene, 2-butene (cis or trans), and 2-methyl propene (isobutylene). Of course, it is understood that mixtures of different olefinic starting materials can be employed, if desired. For example, it is common place to sometimes employ a mixture of 1-butene and 2-butene as the starting olefin. The most preferred olefin is propylene.

Likewise, any conventional rhodium-phosphorus complex catalyst can be employed and such catalyst as well as methods for their preparation are well known in the art. Such rhodium-phosphorus complex catalysts may include any rhodium-organophosphorus complex, such as the rhodium-organophosphine or rhodium-organophosphite complex hydroformylation catalysts heretofore advanced for such hydroformylation processes. Of course, mixtures of such catalysts can also be employed, if desired. Moreover, it is clear that the amount of complex catalyst present in the reaction medium of a given process need only be that minimum amount necessary to provide the rhodium metal concentration desired to be employed and which will furnish the basis for at least that catalytic amount of rhodium metal necessary to catalyze the particular hydroformylation process desired. In general, rhodium metal concentrations in the range of from about 10 ppm to about 1000 ppm, calculated as free metal, should be sufficient for most hydroformylation processes. It is generally preferred to employ from about 10 to 700 ppm of rhodium, and more preferably, from 25 to 500 ppm of rhodium, calculated as free metal.

As noted above, the hydroformylation process of this invention is carried out in the presence of free phosphorus ligand, i.e., ligand that is not complexed with the rhodium complex catalyst employed. However, while it is generally preferred that the free phosphorus ligand be the same as the phosphorus ligand of the rhodium-phosphorus complex catalyst, such is not necessary and different ligands can be employed in a given process, if desired. Accordingly, as in the case of the rhodium-organophosphorus complex catalyst, any conventional organophosphorus ligand can be employed as the free ligand and such ligands, as well as methods for their preparation, are well known in the art. Such free phosphorus ligands may include any of the organophosphine or organophosphite ligands heretofore advanced for such hydroformylation processes. Of course, mixtures of such ligands can also be employed, if desired. Thus, the hydroformylation process of this invention may be carried out in any excess amount of free phosphorus ligand, e.g., at least one mole of free phosphorus ligand per mole of rhodium metal present in the reaction medium. The amount of free phosphorus ligand employed, in general, merely depends upon the aldehyde product desired, and the olefin and complex catalyst employed. Accordingly, amounts of free phosphorus ligand present in the reaction medium ranging from about 2 to about 300 or more per mole of rhodium present should be suitable for most purposes. For example, in general, large amounts of free triarylphosphine ligand, e.g., triphenylphosphine, such as more than 50 moles, or more preferably, more than 100 moles of free ligand per mole of rhodium have preferably been employed to achieve satisfactory catalytic activity and/or catalyst stabilization, while other organophosphorus ligands, e.g., alkylarylphosphines and cycloalkylarylphosphines and/or organophosphites may help provide acceptable catalyst stability and reactivity without unduly retarding the conversion rates of certain olefins to aldehydes when the amount of free ligand present in the reaction medium is as little as 1 to 100 and, more preferably, 15 to 60 moles per mole of rhodium present. More particularly, illustrative rhodium-phosphorus complex catalysts and illustrative free phosphorus ligands include, e.g., those disclosed in U.S. Pat. Nos. 3,527,809; 4,148,830; 4,247,486; 4,283,562; 4,400,548; 4,482,749; 4,496,768; 4,599,206; 4,668,651; 4,716,250; 4,717,775; 4,731,486; 4,737,588; 4,748,261; 4,769,948; 4,744,361; 4,885,401; PCT patent application, Publication No. WO 80/01690 (published Aug. 21, 1980). Among the more preferred ligands and complex catalysts that may be mentioned are, e.g., the triphenylphosphine ligand and rhodium-triphenylphosphine complex catalysts of U.S. Pat. No. 3,527,809 and 4,148,830 and 4,247,486; the alkylphenylphosphine and cycloalkylphenylphosphine ligands, and rhodium-alkylphenylphosphine and rhodium-cycloalkylphenylphosphine complex catalysts of U.S. Pat. No. 4,283,562; and the organophosphite ligands and rhodium-organophosphite complex catalysts of U.S. Pat. Nos. 4,599,206; 4,737,588; 4,717,775; 4,774,361; 4,668,651 and 4,748,261. The most preferred ligand is triphenylphosphine (TPP), while the preferred catalyst is a rhodium-TPP complex.

As further noted above, the hydroformylation reaction is carried out in the presence of higher boiling aldehyde condensation by-products. It is the nature of such continuous hydroformylation reactions employable herein to produce such higher boiling aldehyde by-products (e.g., dimers, trimers and tetramers) in situ during the hydroformylation process as explained more fully, e.g. in U.S. Pat. No. 4,148,830; 4,247,486; and 4,593,127 and U.S. Pat. No.5,001,274. Such aldehyde by-products provide an excellent carrier for the liquid catalyst recycle process. Indeed, while one may employ, if desired, any suitable solvent at the start-up of a continuous process (aldehyde compounds corresponding to the desired aldehyde products being preferred), the primary solvent will normally eventually comprise both aldehyde products and higher boiling aldehyde condensation by-products due to the nature of such continuous processes. Of course, aldehyde condensation by-products can also be performed if desired and used accordingly. It is also obvious that the amount of such higher boiling aldehyde by-products present in the reaction medium may vary over wide limits and is generally governed only by equipment constraints and the particular aldehyde product to be produced. For example, initially the hydroformylation reaction can be effected in the absence or in the presence of small amounts of higher boiling aldehyde condensation by-products as a solvent for the rhodium complex catalyst, or the reaction can be conducted in the presence of upwards of 70 weight percent, or even as much as 90 weight percent, and more of such condensation by-products, based on the total liquid reaction medium. In general, ratios of aldehyde to higher boiling aldehyde condensation by-products within the range of from about 1:4 to about 20:1 by weight should be sufficient for most purposes. Likewise it is to be understood that minor amounts of other conventional organic cosolvents may be present if desired.

While the hydroformylation reaction conditions may very over wide limits, as discussed above, in general it is more preferred that the process be operated at a total gas pressure of hydrogen, carbon monoxide and olefinic unsaturated starting compound of less than about 1500 psia, preferably less than about 450 psia and more preferably less than about 350 psia. The minimum total pressure of the reactants is not particularly critical and is limited mainly only by the amount of reactants necessary to obtain a desired rate of reaction. More specifically, the carbon monoxide partial pressure of the hydroformylation process of this invention is preferably from about 1 to about 120 psia and, more preferably, from about 3 to about 90 psia, while the hydrogen partial pressure is preferably about 10 to about 160 psia and more preferably from abut 15 to about 100 psia. In general $H_2$:CO molar ratio of gaseous hydrogen to carbon monoxide may range from about 1:10 to about 100:1 or higher, the more preferred hydrogen to carbon monoxide molar ratio being from about 1:1 to about 50:1.

Further, as noted above, the hydroformylation process of this invention may be conducted at a reaction temperature from about 50° C. to about 145° C. However, in general, hydroformylations at reaction temperatures of about 60° C. to about 120° C. and more preferably about 75° C. to about 115° C. are preferred.

In one embodiment of this invention, e.g. a continuous hydroformylation liquid recycle system, a portion of the liquid reaction aldehyde product solution containing aldehyde product, solubilized rhodium-phosphorus complex catalyst, free phosphorus ligand and higher boiling aldehyde condensation by-products is removed from the reactor. The desired aldehyde product is separated via vaporization or distillation, in one or more stages, under normal, reduced or elevated pressure from the liquid reaction solution containing both said aldehyde product and solubilized catalyst. The aldehyde product is condensed and collected in a product receiver, and further purified if desired. The remaining non-volatilized catalyst-containing liquid reaction product solution is recycled back to the reactor. Such types of continuous hydroformylation systems and methods for carrying them out are well known in the art and thus need not be particularly detailed herein. Illustrative preferred methods include those illustrated and disclosed, e.g., in U.S. Pat. Nos. 4,148,830 and 4,593,127 and U.S. Pat. No. 5,001,274.

In a preferred embodiment, a solution of rhodium species catalyst in high boiling liquid condensation products together with the aldehyde products resulting from hydroformylation, syn gas, inerts, saturated olefinic by-products, and the like, is removed from the reactor at a rate sufficient to keep a relatively constant level of liquid in the reactor. The aldehyde product effluent stream is heated and the pressure reduced to flash-distill off light gaseous materials, such as unreacted olefin, hydrogen, saturated olefin by-products and the like. Heretofore, the flashed off-gases have generally been compressed and returned to the reactor or merely purged. Due to the large concentration of unreacted olefin contained therein, said flash-distilled off-gas (or vent gas) serves as a preferred gaseous starting material of the subject improvement invention, from which the unreacted olefin is recovered and subsequently recycled to the reactor as outlined herein.

The liquid aldehyde product-catalyst containing stream is then fed to a product separation zone wherein the crude aldehyde product is recovered by conventional techniques, e.g., distillation. Undissolved light gases are also vented off in the product separation zone and may be returned to the reactor, purged or added to the other vent gases and employed as part of the gaseous starting material of the subject improvement invention.

The remaining concentrated catalyst is recycled as a liquid stream to the reaction zone of the reactor and make-up syn gas and olefin are fed into hydroformylation reaction medium, as required. In refining of the crude aldehyde, it is generally further preferred to recycle the light gases dissolved in the crude product to the reactor after their removal via conventional techniques; such as stripping the lights out by passing synthesis gas through the crude product or distillation, although they too may be purged, e.g., burned as fuel, if desired.

Thus it is to be understood that the gaseous effluent starting material containing unreacted carbon monoxide, hydrogen, and olefin, and other lights, e.g., corresponding alkane, of the subject improvement invention can be derived from any appropriate gas vent containing such materials, taken from any suitable location in the hydroformylation reaction system. For example, in addition to the above discussed flash-distilled gas vent stream in a liquid recycle process, a vent line is provided in the head space above the liquid level in the hydroformylation reactor to control the internal pressure build-up in the reactor. This vent line which emerges from the reactor headspace also contains a gaseous mixture of valuable unreacted olefin and syn gas, as well as saturated hydrocarbon and inerts such as nitrogen, carbon dioxide and the like, and may further even contain some gaseous product aldehyde and alcohol by-products. As shown in U.S. Pat. No. 4,593,127, said gaseous vent line in the primary reactor system of FIG. 1 serves to furnish the gaseous starting material for the secondary reactor system, while in the secondary reactor system of FIG. 2, it is purged. On the other hand, the drawings of U.S. Pat. No. 5,001,274, show said gaseous vent line as a means for providing the gaseous starting material of its scrubber which employs the recycled rhodium catalyst solution as its absorbent for the unreacted olefin. Accordingly, said gaseous vent line which emerges from the hydroformylation reactor headspace in this invention may also serve as a means for providing starting material (i.e., gas effluent comprising unreacted olefin, carbon monoxide and hydrogen) for the subject improvement invention from which the unreacted olefin is recovered and subsequently recycled to the reactor as outlined herein.

As described below, in accordance with the present invention, aldehyde product is employed to scrub one or more of the gaseous vent streams of the liquid recycle hydroformylation system to recover unreacted olefin therefrom via absorption of the unreacted olefin in said aldehyde product. In addition to absorbing unreacted olefin, other hydrocarbon gases, such as corresponding alkanes (e.g., ethane in the case of hydroformylating ethylene, propane in the case of hydroformylating propylene and butane in the case of hydroformylating butylene), and gaseous aldehyde, which may be and normally are also present in such vent gas streams, may also be absorbed by the aldehyde product employed as the absorbent liquid in this invention. For example, it is common place to hydroformylate commercial olefin that may already contain some corresponding alkane, while corresponding gaseous alkane is a known by-product such types of hydroformylation. Moreover, an added benefit of the present invention is that such additionally absorbed gases do not have to be separated from the recovered unreacted olefin of the process of this invention prior to recycling said unreacted olefin to the hydroformylation reactor. Any suitable scrubbing (absorption) technique and/or conventional scrubbing (absorption) equipment may be employed herein. For example, such techniques which are designed to recover components from mixed gas streams, in general, preferably involve contacting the gas stream with a suitable liquid solvent (absorbent) in a countercurrent fashion, so as to selectively absorb certain components of the gas into the liquid solvent. The resulting liquid solution is than normally taken to another piece of equipment where the dissolved gases are separated (i.e., desorbed) from the liquid solvent.

Advantages of the present invention include the use of aldehyde product as the liquid solvent (absorbent) along with the fact that extensive additional equipment is not required to remove (i.e., separate) the absorbed unreacted olefin from the resultant scrubbed liquid absorbent. Indeed such is accomplished merely by desorbing (stripping) the absorbed unreacted olefin and other gases from the liquid absorbent with syn gas ($CO+H_2$); no distillation techniques or other additional equipment are required.

For example, referring to the accompanying drawing which schematically shows the present invention, the absorber or scrubber can be a countercurrent type absorption column, (5), wherein contact between the absorbent aldehyde product liquid and gases (unreacted olefin) of the gaseous vent stream or streams is achieved by adding the absorbent or scrubbing liquid to the scrubber at or near the top of the column (line 1) so that it flows downward to its base while the gaseous vent stream or streams (e.g., lines 3 and 4) containing the unreacted olefin enter the side of scrubber at or near its bottom and flow upward. That portion of the scrubbed gaseous stream, e.g., consisting essentially of unreacted carbon monoxide and hydrogen and other light inert components such as methane, nitrogen, carbon dioxide, etc., that is not absorbed by the crude aldehyde product exits at or near the top (line 9) of the column and the resultant crude aldehyde product liquid solution containing the dissolved (absorbed) unreacted olefin, is removed from or near the bottom of the column (line 7).

It is of course to be understood that while the drawing illustrates 2 different gaseous vent lines to the scrubber, e.g., line 4, for conveying the gaseous vent mixture from the headspace of the reactor and line 3 for conveying the gaseous vent mixture flash distilled from the aldehyde product-catalyst effluent removed from the reactor as discussed above, only one such gaseous vent mixture, which is preferably said flash-distilled vent or off-gas of the hydroformylation, is required. Thus, the present invention is not limited by the number of lines conveying the vent gas stream or streams to the scrubber nor by the purity of the aldehyde product. For instance, if desired, said aldehyde product absorbent may be partially purified by passing syn gas through it in a gas stripping column (not shown) to remove some of the residual gases contained in the aldehyde product after it has been separated from the solubilized catalyst containing solution, prior to employing the aldehyde product as the liquid absorbent of this invention. However, while such a purification procedure may be beneficial, it is not a requirement of this invention. Indeed, the subject invention contemplates being able to employ crude aldehyde product, including mixtures of the normal and branched-chain aldehyde products when produced, as the absorbent liquid. Said absorbent liquid requires no further processing after its removal (separation) from the solubilized catalyst containing solution. Further, the present invention also contemplates the possibility of partially condensing one or more of the gaseous vent stream starting materials (e.g., the vent gas from the headspace of the reactor) into a liquid if desired, prior to adding same to the scrubber, e.g., as a mixture along with the absorbent liquid, to help control and obtain preferred lower absorption temperatures in the scrubber. However, such a procedure is not required by the present invention.

The optimum absorption (scrubbing) conditions will of course depend, e.g., upon the particular unreacted olefin and aldehyde product absorbent employed. Generically, the contact time and feed ratio of vent gas to aldehyde product absorbent can each vary widely. Generally, sufficient contact time is maintained to allow for essentially all or at least a major portion of the unreacted olefin of the vent feed gas to be absorbed by the aldehyde product absorbent. Similarly almost any ratio of vent feed gas to aldehyde product absorbent is suitable, so long as the volume of aldehyde product absorbent is sufficient to absorb essentially all or at least a major portion of the unreacted olefin contained in the vent gas. However, it has been found that very good absorption of the unreacted olefin in the aldehyde product can be achieved at very low pressures, i.e., of less than 10 bars. Accordingly, the absorption treatment of this invention may be carried out at a pressure of from about 50 (3.5 bar) to about 140 psia (9.5 bar), preferably from about 80 (5.5 bar), to about 120 psia (8.5 bar), and at a temperature of from about 0° C. to about 60° C., preferably from about 20° C. to about 50° C. Of course, it is further advantageous, for the crude aldehyde product absorbent to have a lower concentration of those components (i.e., unreacted olefin) to be absorbed from the gas stream than the concentration that it would have if it were in equilibrium with the gas stream at the temperature and pressure of the scrubber and at the composition of the gas stream.

This invention is applicable to gas streams containing any concentration of unreacted olefin. Typically such gas streams may contain from about 1 to about 70 percent by weight of unreacted olefin, or higher. While the subject invention may have some utility with gas streams having lower or higher concentrations it may not be economically justified to carry out such a hydroformylation operation. The appropriate ratio of gas stream flow rate to liquid absorbent solution flow rate will vary broadly depending on the compositions, temperatures, and pressures involved. In general a ratio of liquid to gas of from about 0.02 to 1.0 lbs. of liquid per standard cubic foot (SCF) of gas feed should be suitable for most purposes.

As noted the olefin to be hydroformylated according to the liquid recycle process of this invention is an alkylene containing from 2 to 4 carbon atoms. Thus, in the hydroformylation of ethylene the aldehyde product will be a single aldehyde i.e., propionaldehyde (or propanal). On the other hand the hydroformylation of propylene produces a crude product mixture of two butyraldehydes, i.e., normal or straight-chain n-butyraldehyde (n-butanal) and isomer branched-chain iso-butyraldehyde (iso-butanal). Likewise, the hydroformylation of a $C_4$ olefin, e.g., butene-1, butene-2 and isobutene, or mixtures thereof, leads to a crude product mixture of different $C_5$ aldehydes, i.e., normal or straight chain n-valeraldehyde (n-pentanal) and isomer branched-chain, pentanals, i.e. 2-methyl butyraldehyde, 3-methyl butyraldehyde and/or pivaldehyde. Indeed the more preferred hydroformylation processes of this invention are those designed to obtain a high normal to branched-chain aldehyde product mole ratio.

Referring further to the accompanying drawing which schematically shows the present invention, the resultant scrubbed aldehyde product liquid containing the absorbed unreacted olefin, line 7, is pumped (pump, 10) to a countercurrent stripper column 20, wherein contact between the scrubbed aldehyde product and syn gas ($CO+H_2$) is achieved by adding the scrubbed aldehyde product liquid after heating (heater, 15) to the stripper at or near the top of the stripper column 20 so that it flows downward to its base, while fresh syn gas via line 11 enters the stripper column 20 at or near its bottom and flows upward to remove (i.e. desorb or strip) the absorbed unreacted olefin gas from the scrubbed aldehyde product. The gaseous mixture of syn gas and unreacted olefin gas exiting at or near the top of the stripper (line 13) can be directly recycled if desired to the hydroformylation reactor without any further treatment and without requiring any compressor in the recycle line to provide make-up olefin and syn gas for the hydroformylation reaction medium. The resultant stripped aldehyde product liquid (line 17) exits at or near the bottom of the stripper column (20) and may be recovered and/or further purified by any conventional method. For example, in the case of mixed straight-chain and branched-chain aldehyde products, such aldehydes may be separated by distillation, e.g., by the novel distillation method disclosed and discussed in applicant's concurrently filed U.S. application, Ser. No. 611,080 entitled IMPROVED MIXED ALDEHYDE PRODUCT SEPARATION the entire disclosure of which application is encompassed herein by reference thereto. Said novel mixed aldehyde product separation involves obtaining three separate aldehyde product streams from a single distillation column.

A major advantage of the present invention is that conventional gas-liquid stripping techniques and any suitable conventional gas-liquid stripper apparatus may be employed in the present invention. Such provides an economical and simplified means for separating the unreacted olefin from the aldehyde product absorbent that involves the use only of a minimal amount of equipment. However, if desired, the resultant scrubbed aldehyde product containing the absorbed unreacted olefin may first be purified (i.e. desorbed or degassed) of at least a portion of the unreacted olefin in any suitable manner, such as by lowering the pressure and/or raising the temperature just below the boiling point of the resultant aldehyde product absorbent e.g. in a distillation or degassing column, (not shown in the present drawing, but illustrated in U.S. Pat. No. 4,210,426) to separate off gases, such as the unreacted olefin and its corresponding alkane. Subsequently said gases, can be separated, e.g., by use of a separate distillation vessel (not shown in the present drawing but illustrated in U.S. Pat. No. 4,210,426) and the unreacted olefin gas so recovered from its corresponding alkane can be recycled to the hydroformylation reactor. The recovered alkane gas can be purged. The resultant aldehyde product absorbent liquid containing any remaining absorbed unreacted olefin is then fed to the stripper column 20 of the present invention for stripping and recycling of some or all of the unreacted olefin as described herein. For instance if desired the mixture of syn gas and unreacted olefin obtained from the top of the stripper can be cooled and partially condensed and the condensed liquid recycled as desired, e.g. to the hydroformylation reactor or to the above discussed initial distillation or desorbing column (not shown). The remaining non-condensed gases are recycled to the hydroformylation reactor. While such a purification (desorption or degassing) procedure of the scrubbed aldehyde product absorbent prior to its addition to gas stripper of this invention is not required by the present invention, such a procedure may be preferable method for returning essentially only unreacted olefin to the hydroformylation reactor and for controlling unwanted buildup of corresponding alkane gases in said reactor. Indeed, while the present invention includes recycling recovered corresponding alkane gas along with unreacted olefin to the hydroformylation reactor, it is to be understood that unwanted buildup of such corresponding alkane and other undesirable gases in the hydroformylation reactor may be controlled by taking a suitable purge from any recycle line to the reactor or by purging (completely removing from the system) all or part of any gaseous vent stream of the liquid recycle hydroformylation process, e.g., all or part of the vent gas from the headspace of the reactor, or the gaseous vent stream (line 9) taken from the top of scrubber column 5 of the present invention.

The optimum gas stripping conditions will of course depend, e.g., upon the particular unreacted olefin and aldehyde product absorbent employed. Generically the contact time and feed ratio of syn gas to the resultant scrubbed aldehyde product absorbent can each vary widely. Generally sufficient contact time is maintained to allow for essentially all or at least a major portion of the absorbed unreacted olefin of the resultant scrubbed aldehyde product absorbent to be stripped (removed) from said absorbent. Similarly, almost any ratio of syn gas to the resultant scrubbed aldehyde product absorbent is suitable, so long as the volume of syn gas is sufficient to strip (remove) essentially all or at least a major portion of the unreacted olefin contained in the resultant scrubbed aldehyde product absorbent. However, it has been found that very good syn gas stripping of the absorbed unreacted olefin in the resultant scrubbed aldehyde product absorbent can be achieved by carrying out the syn gas stripping treatment of this invention at a pressure of less than about 1500 psia., preferably from about 100 psia to about 500 psia, and more preferably from about 100 psia to about 400 psia, and at a temperature of from about 0° C. to about 130° C., preferably from about 10° C. to about 120° C. In general a ratio of gas to liquid of from about 1 to about 10 standard cubic feet (SCF) of gas per pound of liquid feed should be suitable for most purposes.

Any suitable gas stripping technique and/or conventional gas stripping equipment may be employed herein. For example, such a technique has heretofore been employed in a gas recycle hydroformylation process as seen by *INDICATIONS,* Winter 1982/83, *The International Journal of Davy McKee,* pp. 20 to 28 published by the public affairs department of the Davy Corporation, London, England.

Of course, it is elementary that the hydroformylated aldehyde products have many well-known and conventional utilities. Most preferably, such aldehyde products are further conventionally employed to produce alcohols.

The following examples are illustrative of the present invention and are not to be regarded as limitive. It is to be understood that all parts, percentages and proportions referred to herein and in the appended claims are by weight unless otherwise indicated, the given amount of rhodium being calculated as free metal.

EXAMPLE 1

A computerized simulation (calculated) study is conducted in order to demonstrate the subject invention as follows.

In accordance with the Drawing, gas stream 3 (the flash-distilled off-gas of the catalyst-containing butyraldehyde product effluent stream of a liquid-recycle, rhodium-triphenylphosphine complex catalyzed hydroformylation process of propylene), calculated as containing about 31% by volume propane, about 10% by volume propylene, about 55% by volume mixed butyraldehydes, and the remainder insoluble gases (e.g. nitrogen, CO, hydrogen, etc.) is fed to absorption column 5, which operates at a pressure of about 100 psia and a base temperature of about 47° C. A second vent gas stream 4 is not used in this example. Crude liquid mixed butyraldehyde (stream 1) calculated as containing about 94% by weight mixed normal and isobutyraldehyde at a ratio of about 10 moles normal butyraldehyde to about 1 mole of isobutyraldehyde, about 5% by weight components lighter than isobutyraldehyde (e.g. propylene, propane, etc.), and about 1% by weight components heavier than n-butyraldehyde (n-butanol, butyraldehyde trimer, etc.) is fed counter current to the gas stream at a rate of about 0.27 lbs. liquid/standard cubic foot of total gas feed flow.

The crude aldehyde (stream 1) is introduced at the top of column 5 at a temperature of about 40° C., while gas stream 3 is introduced at the lower side of the column at a temperature of about 47° C. The absorbing column 5 consists of about 1 theoretical tray.

Only about 6.8% by weight of the total propylene introduced via gas stream 3 escapes out vent stream 9. The remainder of the propylene of gas stream 3 (along with propane which is also absorbed) is absorbed in the crude aldehyde absorbent. The resultant aldehyde absorbent stream containing the absorbed propylene along with propane is recovered via line 7 and conveyed by pump 10, heated (heater 15), and is then introduced into a desorber or stripper column (20) wherein a stream (line 11) of syn gas (a mixture of carbon monoxide and hydrogen) is used to desorb (strip out) the propylene from the aldehyde absorbent to obtain a gas mixture of syn gas and propylene (e.g. line 13) and return this mixture to the hydroformylation reactor without the aid of a compressor. In the subject experiment the desorber column (20) operates at a base temperature of about 84° C. and a pressure of about 280 psia. and contains about 5 theoretical stages. The syn gas stream is introduced at a rate of about 1.7 standard cubic feet/lb. of the liquid propylene-containing aldehyde absorbent feed to the column. The amount of propylene recycled to the hydroformylation reactor is essentially equal to the total amount of propylene in gas stream 3 minus that amount of propylene which may escape the system via stream 9, and via the resultant stripped aldehyde product liquid (line 17) that is obtained from the desorber column (20). About 4% by weight of the propylene fed to the desorber column (20) is lost out of the bottom of said desorber column (e.g. via line 17).

EXAMPLE 2

In accordance with the Drawing, gas stream 3 (the flash-distilled off-gas of the catalyst-containing butyraldehyde product effluent stream of a liquid-recycle, rhodium-triphenylphosphine complex catalyzed hydroformylation process of propylene), containing about 32% by volume propane, about 33% by volume propylene, about 1% by volume mixed butyraldehydes, and the remainder insoluble gases (e.g. nitrogen, CO, hydrogen, etc.) and a second vent gas stream 4 (the gaseous vent stream taken from the reactor headspace of said hydroformylation process), containing about 47% by volume propane, about 44% by volume propylene, and about 1% by volume mixed butyraldehydes (balance insoluble gases), were fed to absorption column 5, which was operated at a pressure of about 114 psia and a base temperature of about 40° C. Crude liquid mixed butyraldehyde (stream 1) containing about 99.5% by weight mixed normal and iso-butyraldehyde at a ratio of about 10 moles normal butyraldehyde to about 1 mole isobutyraldehyde, about 0.1% by weight components lighter than isobutyraldehyde (e.g. propylene, propane, etc.), and about 0.4% by weight components heavier than n-butyraldehyde (n-butanol, butyraldehyde trimer, etc.) was fed counter current to the gas streams at a rate of about 0.07 lbs. liquid/standard cubic foot of total gas feed flow.

The crude aldehyde (stream 1) was introduced at the top of column 5 at a temperature of about 25° C., while the gas streams 3 and 4 were introduced at the lower side of the column at temperatures of about 31° C. and about 40° C., respectively. The absorbing column 5 consisted of about 10 theoretical trays, with water-cooled intercondensers as trays 4 and 8 (from the top of the column).

Only about 1.8% by weight of the total propylene introduced via gas streams 3 and 4 escaped out vent stream 9. The remainder of the propylene of gas streams 3 and 4 (along with propane which was also absorbed) was absorbed in the crude aldehyde absorbent. The resultant aldehyde absorbent stream containing the absorbed propylene along with propane was recovered via line 7 and conveyed by pump 10 to an optional distillation column (not shown) in order to obtain part of the absorbed propylene by conventional distillation, which was operated at a top temperature of about 60° C. and a base pressure of about 367 psia. A gaseous propylene enriched stream containing propylene in an amount equal to about 3.9% by weight of the total amount of propylene contained in gas streams 3 and 4 was taken off the top of said distillation column. Said gaseous propylene-enriched stream was then treated in a second optional distillation column (not shown) wherein the propane was conventionally fractionally distilled from the propylene that was present. The gaseous propylene-containing stream so obtained was returned to the hydroformylation reactor without the aid of a compressor. This second distillation column was operated at a pressure of about 360 psia and a top temperature of about 58° C. Greater than 99% by weight of the propylene in said propylene-enriched gas stream from the first distillation column was returned to the hydroformylation zone. The propane recovered from the bottom of the second distillation column was purged from the system.

The remaining propylene-containing liquid aldehyde absorbent stream recovered from the bottom of said first distillation column was then heated (e.g. heater 15) and introduced into a desorber or striper column (e.g. column 20) wherein a stream (e.g. line 11) of syn gas (a mixture of carbon monoxide and hydrogen) was used to desorb (strip out) the propylene from the aldehyde absorbent to obtain a gas mixture of syn gas and propylene (e.g. line 13). In the subject experiment the desorber column was operated at a base temperature of about 78° C. and a pressure of about 295 psia. and contained about 9 theoretical stages. The syn gas stream was introduced at a rate of about 2.0 standard cubic feet/lb. of the liquid propylene-containing aldehyde absorbent feed to the column. The overhead gaseous stream of mixed syn gas and propylene (e.g. line 13) was cooled to 31° C. to condense part of the gaseous stream in a vessel (not shown), the condensed liquid being recycled by a line (not shown) to absorbent stream 7 obtained from absorber 5. The resultant separated non-condensed gaseous stream of mixed syn gas and propylene was returned via a recycle line (not shown) to the hydroformylation reactor. The amount of propylene so recycled was essentially equal to the total amount of propylene in gas streams 3 and 4 minus that amount of propylene already recycled via the gaseous overhead of said first distillation column and that amount which may have escaped the system via stream 9, via the propane recovered from the bottom of said second distillation column, and via the resultant stripped aldehyde product liquid (e.g. line 17) obtained from the desorber column (e.g. 20). Less than about 0.5% by weight of the propylene fed to the desorber column (e.g. 20) was lost out of the bottom of said desorber column (e.g. via line 17).

Various modifications and variations of this invention will be obvious to a worker skilled in the art and it is to be understood that such modifications and variations are within the purview of this application and the spirit and scope of the appended claims.

What is claimed is:

1. In an improved liquid recycle rhodium-catalyzed hydroformylation process for producing $C_3$ to $C_5$ aldehydes, wherein an olefin containing from 2 to 4 carbon atoms, carbon monoxide and hydrogen are reacted in the presence of a solubilized rhodium-phosphorus complex catalyst, free phosphorus ligand and higher boiling aldehyde condensation by-products, to produce an aldehyde product selected from the class consisting of propanal, a mixture of n-butanal and iso-butanal, and a mixture of n-pentanal and branched-chain pentanals, and wherein a gaseous effluent comprising unreacted olefin, carbon monoxide and hydrogen gases is vented from the process, the improvement which comprises recovering said unreacted olefin from said vent gas by (1) absorbing the unreacted olefin in an absorbent comprising the liquid aldehyde product produced by said hydroformylation process and wherein the absorption treatment is carried out at a pressure of from 3.5 bar to about 9.5 bar and at a temperature of from about 0° C. to about 60° C.; (2) stripping the absorbed unreacted olefin from said absorbent by passing synthesis gas through the resultant absorbent containing said unreacted olefin to obtain a gaseous mixture of synthesis gas and the stripped unreacted olefin and wherein the stripping treatment is carried out at a pressure of from about 100 psia to about 500 psia and at a temperature of from about 0° C. to about 130° C.; and (3) recycling said gaseous mixture to the hydroformylation reactor of said hydroformylation process.

2. A process as defined in claim 1, wherein the unreacted olefin is ethylene and the aldehyde product is propanal.

3. A process as defined in claim 1, wherein the unreacted olefin is propylene and the aldehyde product is a mixture of n-butanal and iso-butanal.

4. A process as defined in claim 1 wherein the olefin is butene and the aldehyde product is a mixture of n-pentanal and branched chain pentanals.

5. A process as defined in claim 3 wherein the phosphorus ligand of the rhodium complex catalyst and the free phosphorus ligand of the hydroformylation process is triphenylphosphine.

6. A process as defined in claim 5 wherein the absorption treatment of step (1) is carried out at a pressure of from about 5.5 bar to about 8.5 bar and at a temperature of from about 20° C. to about 50° C.

7. A process as defined in claim 6 wherein the stripping treatment of step (2) is carried out at a pressure of from about 100 psia to about 400 psia and at a temperature of from about 10° C. to about 120° C.

* * * * *